United States Patent [19]

Horikami

[11] Patent Number: 5,148,375
[45] Date of Patent: Sep. 15, 1992

[54] SOLDERING APPEARANCE INSPECTION APPARATUS

[75] Inventor: Kinji Horikami, Suita, Japan

[73] Assignee: Matsushita Electric Industrial Co., Ltd., Osaka, Japan

[21] Appl. No.: 613,990

[22] Filed: Nov. 15, 1990

[30] Foreign Application Priority Data

Nov. 17, 1989 [JP] Japan .................. 1-300443

[51] Int. Cl.$^5$ ............................. G06F 15/46
[52] U.S. Cl. .................. 364/552; 364/507; 382/8; 358/106
[58] Field of Search ............ 364/552, 551.01, 550, 364/506, 507; 382/8; 356/237; 358/106

[56] References Cited

U.S. PATENT DOCUMENTS

| | | | |
|---|---|---|---|
| 4,454,585 | 6/1984 | Ele | 364/552 |
| 4,772,125 | 9/1988 | Yoshimura et al. | 358/106 |
| 4,878,114 | 10/1989 | Huynh et al. | 364/551.01 |
| 4,942,618 | 7/1990 | Sumi et al. | 382/8 |
| 4,974,261 | 11/1990 | Nakahara et al. | 356/237 |
| 4,988,202 | 1/1991 | Nayar et al. | 358/106 |
| 4,999,785 | 3/1991 | Schmuter | 364/507 |

Primary Examiner—Parshotam S. Lall
Assistant Examiner—Michael J. Zanelli
Attorney, Agent, or Firm—Wenderoth, Lind & Ponack

[57] ABSTRACT

A soldering appearance inspection apparatus is for detecting a faulty soldering at a soldered portion on a printed circuit board. The inspection apparatus includes an illuminating device for illuminating the soldered portion, an image pickup device for picking up an image of the soldered portion, a position detecting device for detecting the position of the soldered portion from the picked up image, and a soldered state judging device for judging an excess or insufficiency of the amount of solder, and also for judging a presence or absence of scorching and luster at the soldered portion, based on a ratio of a region of light subjected to regular reflection on the solder to a size of the soldered portion.

4 Claims, 6 Drawing Sheets

GOOD SOLDERING

INSUFFICIENT SOLDER

EXCESSIVE SOLDER

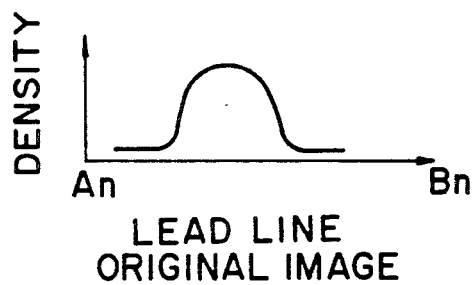
Fig. 8(a) LEAD LINE ORIGINAL IMAGE
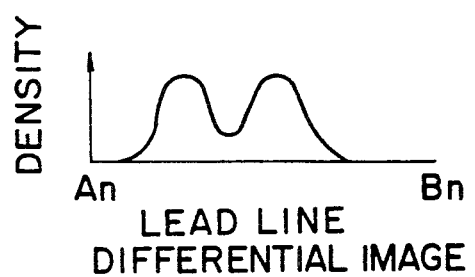
Fig. 8(b) LEAD LINE DIFFERENTIAL IMAGE
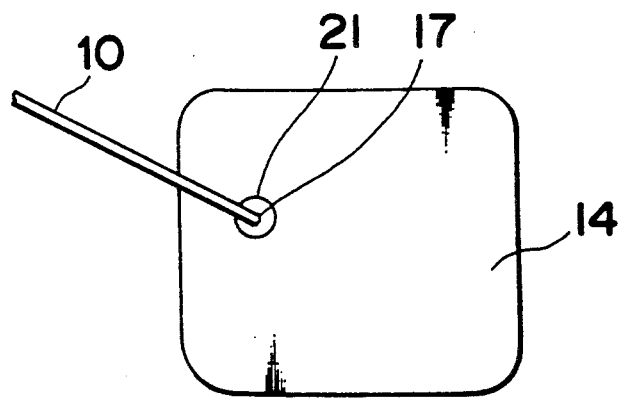
Fig. 9

5,148,375

SOLDERING APPEARANCE INSPECTION APPARATUS

BACKGROUND OF THE INVENTION

The present invention generally relates to an examining apparatus, and more particularly, to a soldering appearance inspection apparatus for automatically examining whether or not lead wires are properly soldered onto soldering portions of a printed circuit board or the like.

Recently, there have been proposed various kinds of soldering appearance inspection apparatuses for the purpose as described above. The conventional inspection apparatus for discriminating good products by obtaining a three-dimensional shape of a soldered portion by a light ray cutting system as disclosed, for example, in Japanese Patent Laid-Open Publication Tokkai-sho No. 63-196980, has been so arranged to effect the judgement by comparing a histogram in dark/light image of the solder and its binary coded image over a predetermined threshold value, with those of a good product. However, the above known arrangement requires a long processing time, while a photo-detector having a large dynamic range as referred to therein is necessary, and thus, this apparatus is not suitable for practical applications. There has also been conventionally proposed in Japanese Patent Laid-Open Publication Tokkaisho No. 64-68606, an inspection apparatus for judging a quality of soldering through utilization of the fact that, upon projection of a concentric multi-circular pattern light onto a soldered portion, the multi-circular pattern image is distorted when the configuration of the soldered portion is abnormal. Another known apparatus disclosed, for example, in Japanese Patent Laid-Open Publication Tokkaisho No. 64-73207 is so arranged that by once projecting ring-shaped pattern light onto a printed circuit board, a judgement is made as to whether or not the solder configuration is good by a distance between a high brightness portion formed by reflection of its indirect light on a soldered face and a lead wire.

However, in the conventional soldering appearance inspection apparatuses as referred to above, although the solder configurations may be compared with those on a good printed circuit board in the case where scattering in the sizes and positions of soldered portions and lead wires to be examined is small, it has been difficult to inspect soldering appearance of a printed circuit board in which positions and sizes of soldered portion are scattered or lead wires are merely soldered onto land portions without the presence of any through-holes.

Similarly, it has also been difficult to detect a faulty state such as scorching or no luster on the surfaces of the soldered portions by the partial pattern light projecting method.

SUMMARY OF THE INVENTION

Accordingly, an essential object of the present invention is to provide a soldering appearance inspection apparatus which is capable of judging the quality of soldering at soldered portions on a printed circuit board such as excessive or insufficient amount of solder, presence of luster or scorching on the surfaces of the soldered portions even when positions and sizes of the soldered portions are varied on the printed circuit board.

A second object of the present invention is to provide a soldering appearance inspection apparatus of the above described type, which is capable of detecting the quality of soldering of lead wires based on an intruding position of the lead wire into the solder.

A third object of the present invention is to provide a soldering appearance inspection apparatus of the above described type, which is capable of detecting the presence of a tunnel-like cavity which gives rise to the possibility of disengagement or slipping off of the lead wire at the lead wire intruding position in the solder.

A fourth object of the present invention is to provide a soldering appearance inspection apparatus of the above described type, which is capable of detecting a lead wire remaining or protruding state in which an unnecessary end portion of the lead wire projects out of the soldered portion for possible short-circuiting or the like.

In accomplishing these and other objects, according to one aspect of the present invention, there is provided a soldering appearance inspection apparatus for detecting faulty soldering at soldered portions on a printed circuit board and the like such as an excessive or insufficient amount of solder during soldering of lead wires at soldering portions on the printed circuit board, faulty lead wire positions, tunnel-like cavities formed in solder at lead wire intruding positions and remaining lead wires by projection of lead wire ends out of solder, etc. The inspection apparatus includes an illuminating means for illuminating the soldered portion, an image pickup means for picking up an image of the soldered portion, a position detecting means for detecting the position of the soldered portion from the picked up image, and a soldered state judging means for judging an excess or insufficiency of the amount of solder, and also for judging a presence or absence of scorching and luster at the soldered portion based on a ratio of a region of light subjected to regular reflection on the solder, to a size of the soldered portion.

In the second aspect of the present invention, the soldering appearance inspection apparatus of the first aspect further includes a lead wire position detecting means for detecting an intruding position and direction of the lead wire at an outer side portion of the solder, a differentiation processing means for obtaining an absolute value of variation in brightness of the lead wire, a lead wire intruding position detecting means for detecting the intruding position of the lead wire into the solder through pursuit of bottoms between crests indicating variation of brightness, and a lead wire soldered state discriminating means for discriminating quality of the lead wire soldered state based on the lead wire intruding position with respect to the soldered portion.

In the third aspect of the present invention, the soldering appearance inspection apparatus of the first aspect further includes a binary coding means for binary coding a partial region centered at the lead wire intruding position by an intermediate value of brightness of the solder and concave portion at a position where the lead wire intrudes into the solder, means for obtaining binary projection at said partial region, and judging means which obtains size and degree of circularity of said concave portion darkened by the binary coding based on maximum and minimum values of data obtained by dividing projecting axis at least into three equal portions for judging whether or not said concave portion is of a tunnel-like cavity.

In the fourth aspect of the present invention, the soldering appearance inspection apparatus of the first aspect further includes a differentiation processing means for obtaining a variation of brightness of the lead wire, a binary coding means for binary coding the differentiation processed image at levels higher than a predetermined level, and a remaining wire detecting means for judging a presence or absence of a binary image configuration having a feature of a lead wire located outside the solder and present at portion different from the lead wire position.

By the first aspect of the present invention as referred to above, since the ratio of the regular reflection region for determining the quality of the soldered state with respect to the size of the soldered portion is obtained through detection of the soldered position, faulty soldering which may result in the poor contacts of the lead wires such as excessive or insufficient amount of the solder, no luster on the surface, scorching, etc. may be prevented without being affected by the scattering of the sizes and positions of the soldered portions.

According to the second aspect of the present invention, since the lead wire intruding position into the soldering portion is obtained, the length through which the lead wire is soldered may be found, and it becomes possible to prevent disengagement or poor contact of the lead wire.

By the third aspect of the present invention, due to the detection of the state of the tunnel-like cavity at the lead wire intruding position, faults such as slipping off of lead wires, etc. may be prevented.

Furthermore, by the fourth aspect of the present invention, unnecessary remaining ends of the lead wires may be detected, and therefore, a short-circuit with respect to other land portions or casing, etc. due to a remaining lead wire, can also be prevented.

BRIEF DESCRIPTION OF THE DRAWINGS

These and other objects and features of the present invention will become apparent from the following description taken in conjunction with the preferred embodiment thereof with reference to the accompanying drawings, in which;

FIGS. 8(a) and 8(b) are diagrams showing density distributions in the lead wire detecting range, FIG. 9 is a diagram similar to FIG. 3, which particularly relates to detection of a tunnel-like cavity according to a third embodiment of the present invention.

DETAILED DESCRIPTION OF THE INVENTION

Figure 1:
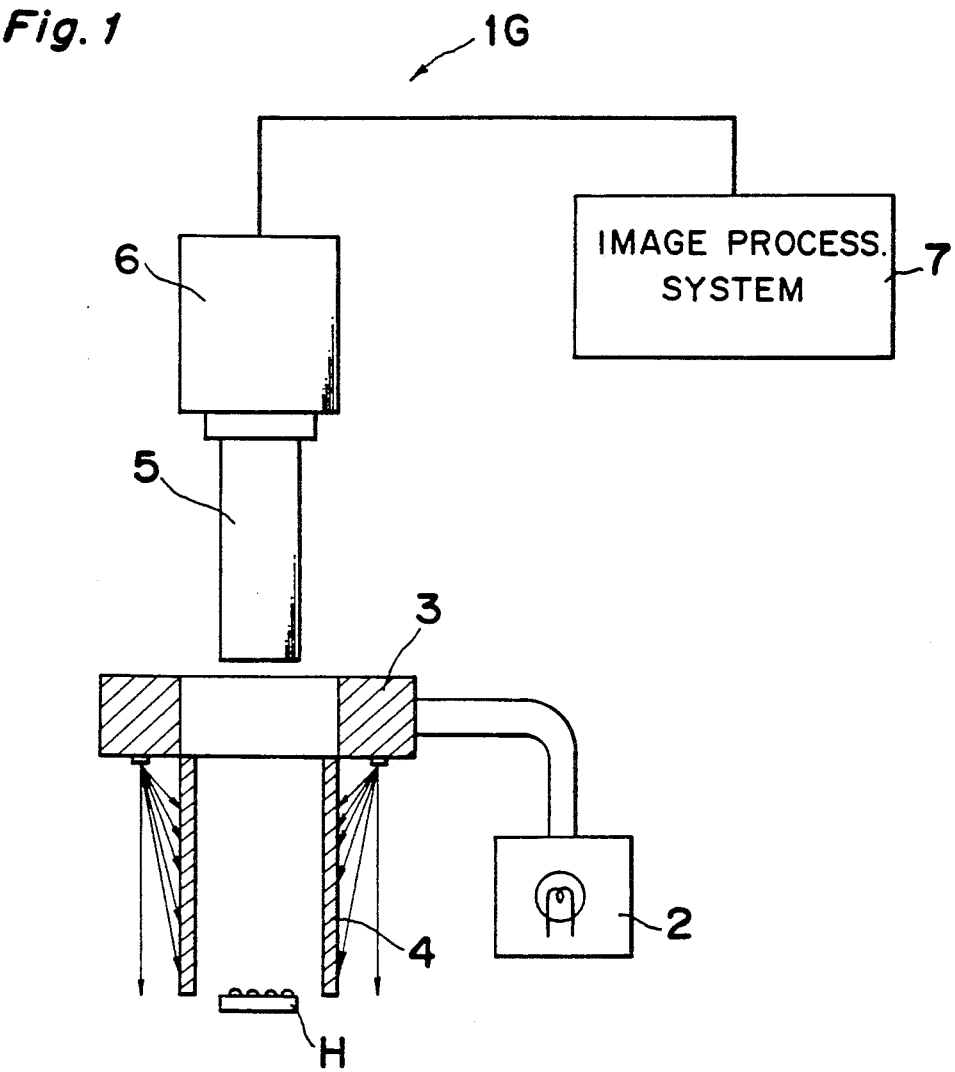
FIG. 1 is a schematic diagram showing a general construction of a soldering appearance inspection apparatus according to one preferred embodiment of the present invention.

Before the description of the present invention proceeds, it is to be noted that like parts are designated by like reference numerals throughout the accompanying drawings.

First embodiment

Referring now to the drawings, there is shown in FIG. 1 a soldering appearance inspection apparatus 1G for automatically determining whether or not lead wires are properly soldered onto soldering portions of a printed circuit board or the like.

In FIG. 1, the inspection apparatus 1G generally includes an illuminating light source 2 for illuminating an object to be examined, e.g. a video head H, a ring-light guide 3 for irradiating light rays from the light source 2 in a ring-like configuration, a diffusing cylinder 4 provided below the ring-light guide 3 for diffusing the light rays irradiated from the ring-light guide 3 so as to produce soft illumination within the cylinder 4 for the video head H to be examined, a television camera 6 (referred to as a TV camera hereinafter) disposed above said ring-light guide 3, with its lens assembly 5 for picking up an enlarged image of the video head H being provided above and adjacent to the ring-light guide 3 as illustrated, and an image processing system 7 coupled with the TV camera 6 for judging a quality of the soldering through processing of the signal of the picked-up image.

Figure 2:
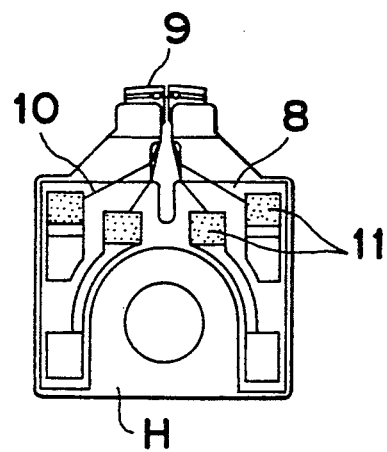
FIG. 2 is a top plan view showing, on an enlarged scale, a video head to be inspected by the inspection apparatus of FIG. 1.

FIG. 2 is an enlarged and detailed view of the video head H to be examined. The video head H includes a printed circuit board 8 affixed thereto, through a base 12(FIG. 3), a core portion 9, lead wires 10 led from a coil (not particularly shown) wound on the core portion 9, and soldered portions 11 on the printed circuit board 8 to which the lead wires 10 are connected. On the printed circuit board 8 of the video head H, four soldered portions 11 to be examined are formed as is seen from FIG. 2. Since a visual field 16 to be picked up by the TV camera 6 is enlarged by the lens assembly 5, one of the soldered portions 11 is brought into the visual field. Thus, by moving the TV camera 6, examination of the soldering appearance at the four soldering portions 11 may be effected.

The judgement as to quality of the soldered state is to be effected based on a principle as explained hereinafter with reference to FIG. 3 and FIGS. 4(a) to 4(c).

Figure 3:
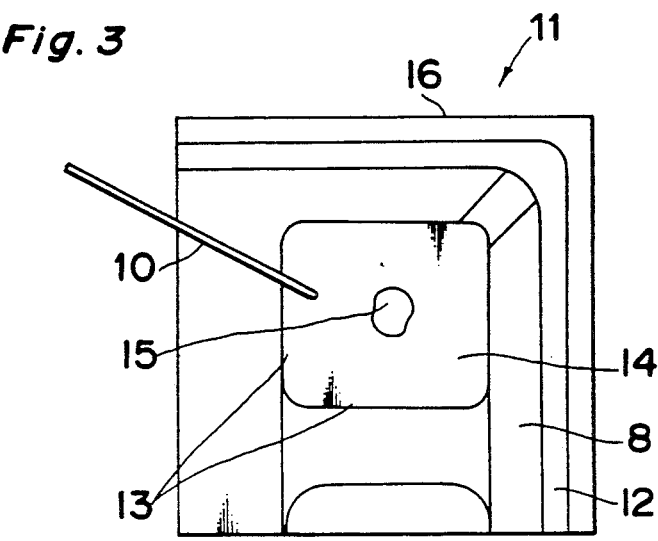
FIG. 3 is a top plan view showing, on an enlarged scale, one of soldered portions on the video head of FIG. 2, as picked up by a TV camera shown in FIG. 1, FIGS. 4(a) to 4(c) are diagrams showing principles for the judgement of quality of the state of soldering by the inspection apparatus of FIG. 1.
Figure 4A:
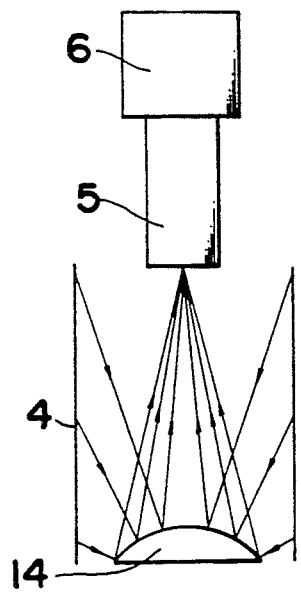
Figure 4A:
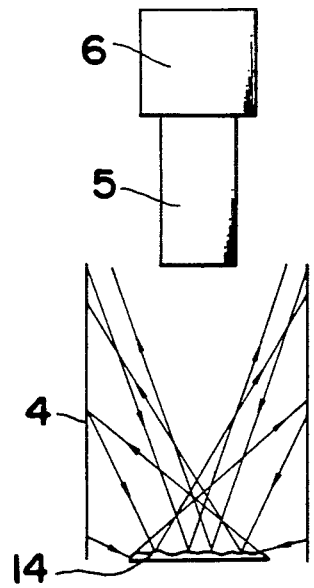
Figure 4A:
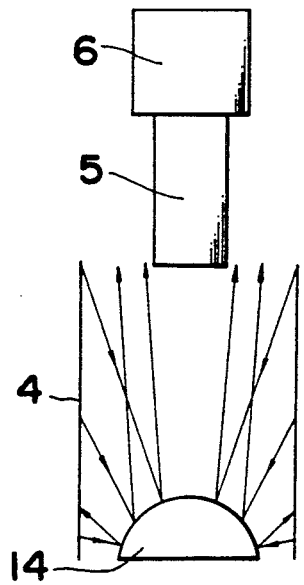

In the soft light irradiated from the diffusion cylinder 4, regular reflection light thereof is concentrated on the lens assembly 5 as shown in FIG. 4(a) when the soldering is in a good state, and the solder 14 shown in the soldered portion 11 of FIG. 3 is picked up by the TV camera 6 in a bright state on the whole except for an optically dark portion 15. However, in the case where the amount of solder is insufficient or excessive, the surface of the soldered portion 11 takes a shape by which the regular reflection light is not incident upon the lens assembly 5 as shown in FIG. 4(b) or 4(c), and thus, the solder 14 is picked up to be dark on the whole. Meanwhile, when the surface of the solder 14 has no luster or has scorching thereon, reflectance on the surface is deteriorated, and therefore, even when the solder configuration is as shown in FIG. 4(a), the solder 14 is picked up to be dark by the TV camera 6.

Figure 5:
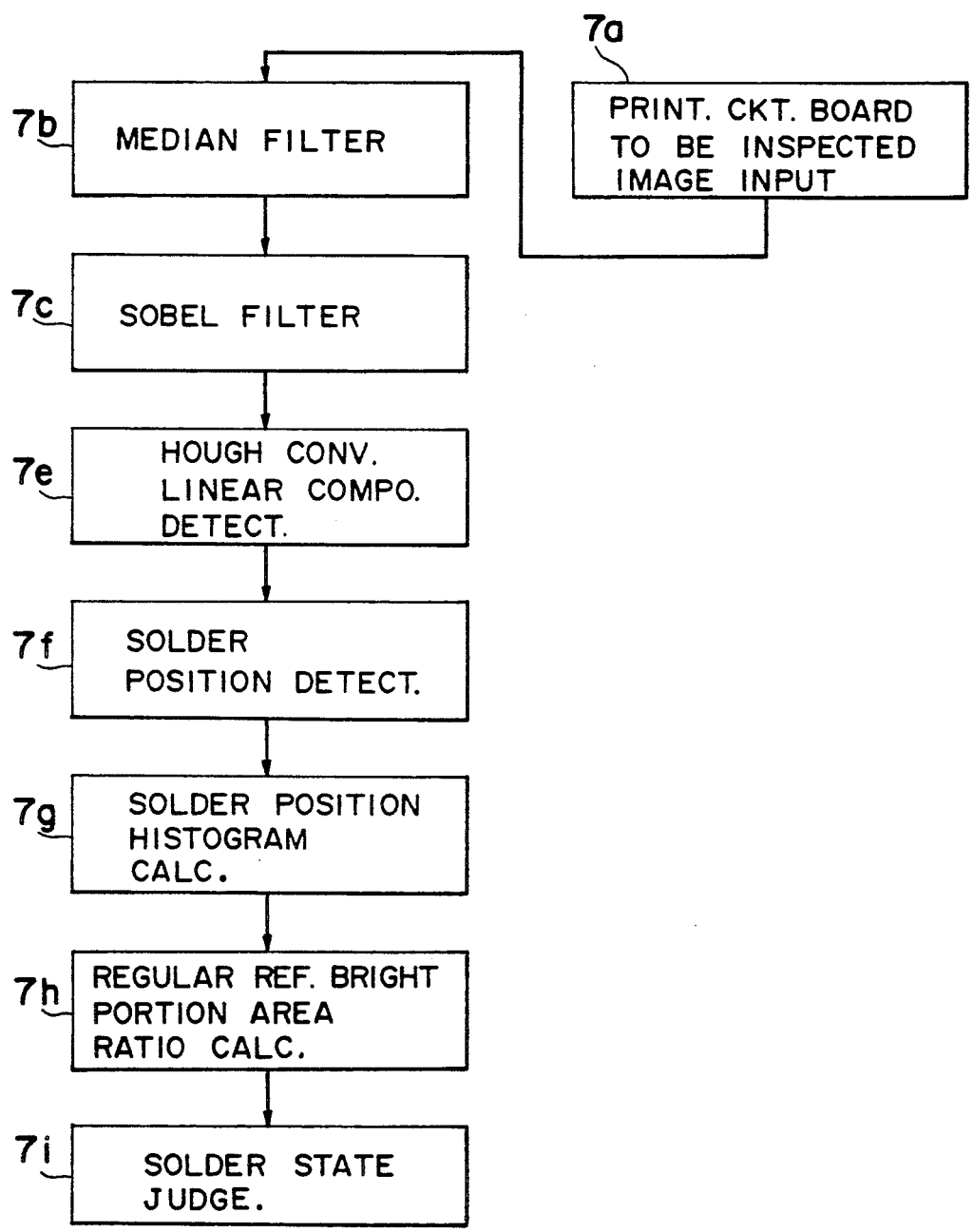
FIG. 5 is a flow-chart showing steps of the soldering appearance inspection at an image processing system in FIG. 1.

Referring to a flow-chart of FIG. 5, the soldering appearance inspection operation in the image processing system 7 will be described. In the first place, at Step 7a, image input of the printed circuit board to be examined is effected to obtain an image similar to that shown in FIG. 3. Then, at Step 7b, the image is passed through a median filter (not shown) to remove a noise component from the image. The image thus processed is formed at Step 7c into a differentiation image whose density becomes high in the presence of variation in brightness by a sobel filter (not shown). Moreover, in the image thus obtained, a linear component detection is effected through employment of a Hough conversion at Step 7e. Although some linear components are normally present in the image, portions in the vicinity of edges showing linear components other than those of the solder 14 are all of the equal density regions with constant brightness, and therefore, they may be distinguished from a solder edge 13. Thus, in the solder position detection at Step 7f, the position of the solder edge 13 may be obtained with respect to the four sides. Subsequently, at Step 7g, histogram calculation for the region surrounded by the solder edge 13 is effected. At Step 7h, through utilization of the fact that the regular reflection brightness portion has the cumulative frequency equivalent to that above a certain threshold value of the histogram, an area ratio in the region of the solder edge 13 of the regular reflection brightness portion is calculated. At Step 7i, a judgement of the soldering state is effected based on the calculated area ratio.

As is seen from the foregoing description, according to the above embodiment, by providing the illuminating means for illuminating the solder 14, the position detecting means for detecting the position of the soldered portion, and the soldered state judging means for judging the quality of the soldering based on the ratio of the area for the regular reflection brightness portion with respect to the size of the soldered portion, it becomes possible to identify an excess or insufficiency in the amount of solder and the soldered state such as no luster or presence of scorching on the surface of the soldered portion so as to prevent products with such faulty soldering from proceeding into subsequent processes. Normally, the products judged to be faulty are rectified through repeated soldering, etc.

Second embodiment

Figure 6:
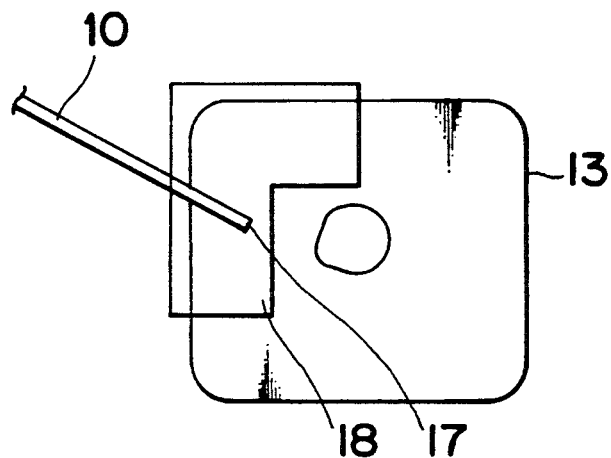
FIG. 6 is a processed image diagram similar to FIG. 3, which particularly relates to a lead wire intruding position detection according to a second embodiment of the present invention.

FIG. 6 shows a diagram representing a processed image according to the second embodiment of the present invention.

The processed image in FIG. 6 is a differentiation processed image arranged to be raised in density in the presence of a variation of brightness as explained earlier with reference to the first embodiment. In FIG. 6, Numeral 17 represents a lead wire intruding position at which the lead wire 10 intrudes into the solder 14, while Numeral 18 denotes a lead wire intruding position permissible area relatively positioned with respect to the solder edge 13.

Figure 7:
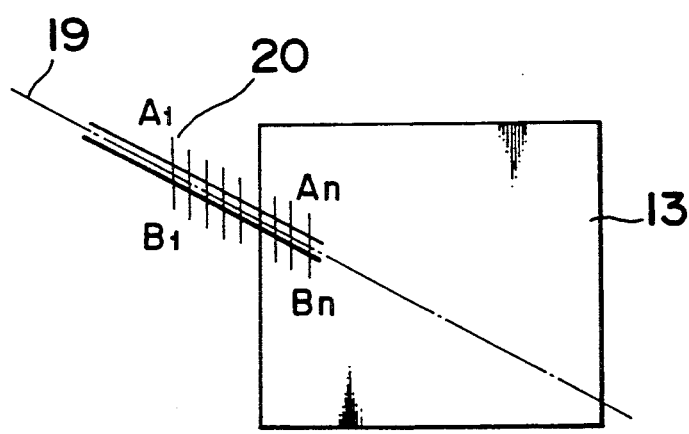
FIG. 7 is a diagram for explaining the lead wire intruding position detection.

Meanwhile, in a diagram of FIG. 7 which denotes means for detecting the lead wire intruding position 17, Numeral 19 represents the position of the lead wire, and Numeral 20 indicates a lead wire detecting range for searching for the lead wire intruding position 17 along the lead wire position 19. FIG. 8(a) is a graphical diagram showing a relation between the lead wire original image and density variation of the lead wire from a start point An to an end point Bn in the lead wire detecting range, while FIG. 8(b) is also a graphical diagram showing a lead wire differentiation image which represents a differentiation processed image thereof.

As shown in FIG. 7, the solder edge 13 is obtained by the means as explained earlier with reference to the first embodiment. The lead wire 10 is detected in its angle and position as in the lead wire position 19 in the form of a linear component through the Hough conversion at the outer side of the solder edge 13. When the density distribution in the lead wire detecting range 20 is checked along the lead wire position 19, the curve takes a form as in FIG. 8(b) in which there are two crests with a bottom therebetween. Here, the image dealt with by the lead wire detecting range 20 is of a differential image as shown in FIG. 6. Through pursuit of the bottom portions in the density distribution to be obtained by the lead wire detecting range 20, the position where the bottom portions disappear is detected as the lead wire intruding position 17. When the lead wire intruding position 17 is located within the lead wire intruding position permissible area 18 relatively positioned with respect to the solder edge 13, the lead wire is judged to be in a good soldered state, while, when it is out of the permissible area 18, the soldered state of the lead wire is graded as faulty.

Accordingly, by the second embodiment of the present invention as described so far, in addition to the effect available in the first embodiment, it becomes possible to judge the quality of the soldered state of the lead wire from the lead wire intruding position 17.

Third embodiment

Figure 10:
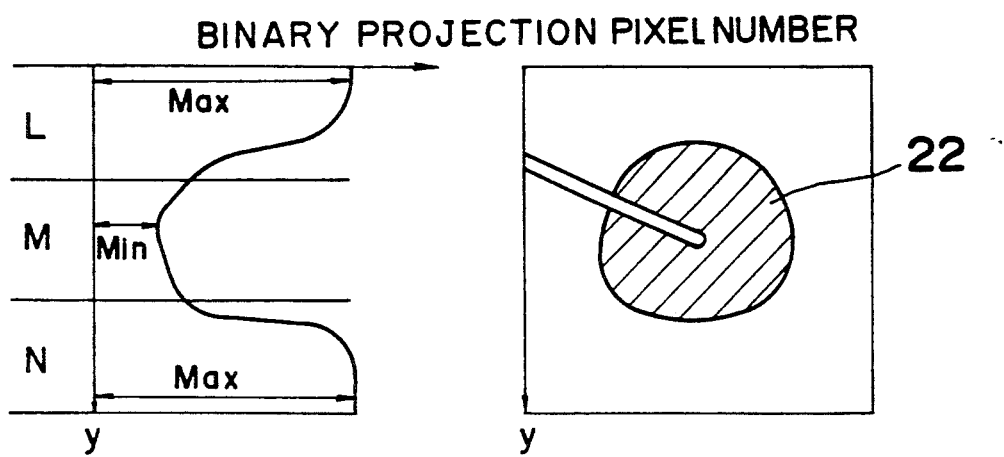
FIG. 10 is a diagram for explaining detection of the tunnel-like cavity.

FIG. 9 is a schematic diagram for explaining a tunnel-like cavity related to a third embodiment of the present invention, and FIG. 10 is also a diagram for explaining means for detecting such a tunnel-like cavity.

In FIG. 9, Numeral 21 represents a tunnel-like cavity formed by non-fusing of the solder 14 around the lead wire 10 at the lead wire intruding position 17. FIG. 10 shows a binary image obtained by binary coding the signal of the image picked up by the TV camera in the form of a recess through illumination by the illuminating means as explained in the first embodiment, by an intermediate value of brightness between the recess and the solder, and also shows a binary projection graph with respect to the y axis. Numeral 22 represents the recess darkened by the binary coding.

In the first place, since the lead wire intruding position 17 has already been found by the means described earlier with reference to the second embodiment, a partial region of a size capable of extracting the recess 22 is provided by setting the lead wire intruding position 17 as a center. By effecting a histogram calculation within the partial region, an intermediate value between a crest indicating brightness at the recess portion is obtained as a binary coded threshold value. Through employment of the binary coded threshold value, binary projection of the image in the binary coded partial region with respect to the y axis is effeced. The result will be represented by the graph as shown in FIG. 10, and its projection axis is divided into three equal zones respectively represented as L, M and N, and in the L and N zones, the maximum value of the binary projection pixel number is obtained, while, in the M zone, the minimum value thereof is obtained. In the presence of the recess 22, there is a large difference, in the binary projection pixel number, between the maximum value in the L and N zones and the minimum value in the M zone, whereas, if there is hardly present any recess 22, the difference as above will also be reduced to almost nil. Thus, in order to see whether or not the recess 22 is of a tunnel-like cavity 21, it is possible to judge a presence or absence of the tunnel-like cavity 21 through comparison with the difference value between the maximum value and minimum value of the binary projection pixel number in the limited samples.

Therefore, by the third embodiment of the present invention as described above, in addition to the effect obtained by the first embodiment, it is possible to judge whether or not the recess at the lead wire intruding position is of a tunnel-like cavity, and accordingly, video heads having a possibility of the lead wire slipping off or poor contact may be prevented from being fed to subsequent processes.

Fourth embodiment

Figure 11:
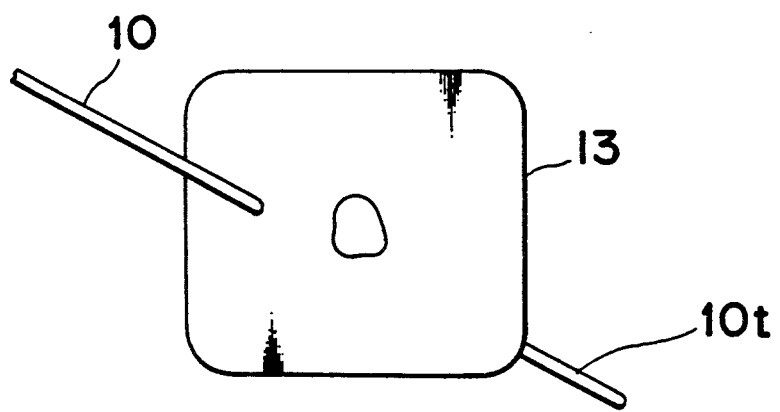
FIG. 11 is a diagram similar to FIG. 3, which particularly relates to detection of remaining lead wire ends according to a fourth embodiment of the present invention.

FIG. 11 is a schematic diagram for explaining a remaining lead wire related to a fourth embodiment of the present invention.

In FIG. 11, a terminal end portion 10t of the lead wire 10 is protruding or projecting out of the solder edge 13 to show the state of the remaining lead wire.

The image in FIG. 11 is one obtained by binary coding the differential processed image explained earlier with reference to the first embodiment by such a threshold value as will form the lead wire 10 into one white line. Since the regular position of the lead wire 10 and the solder edge 13 are already found by the means described earlier with reference to the embodiments 1 and 2, it is judged whether or not any binary image configuration having features of the lead wire located in position other than the above is present. More specifically, after masking the lead wire 10 and the solder edge 13, characteristic values such as the area and secondary moment, etc. of the binary image configuration in the remaining region are measured, and if there is any characteristic value closely in agreement with the characteristic value of the lead wire, it is judged that the remainder or end 10t of the lead wire is present.

Therefore, by the fourth embodiment of the present invention as described so far, in addition to the effect available by the first embodiment, it becomes possible to detect the remaining lead wire, and video heads having an unnecessary remaining lead wire which can possibly give rise to a short-circuit or the like can be prevented from being fed into subsequent processes.

It is to be noted here that, in the first embodiment, although the linear component detection is effected for the soldered position detection, the solder edge 13 is not limited, in its configuration, to be rectangular, but may for example, be in an arcuate shape. Since the solder edge may be found by the arcuate component detection even in the above case, the kinds of shapes of the objects to be dealt with for finding the soldered position according to the present invention are not limited.

As is clear from the foregoing description, by the first embodiment of the present invention, since it is possible to judge the quality of the soldering by detecting the soldered position, and obtaining the area ratio of the regular reflection region from the solder surface at said soldered position, faulty soldering which may result in the poor contacts of the lead wires such as excessive or insufficient amount of the solder, no luster on the surface, scorching, etc. may be prevented without being affected by the scattering of the sizes and positions of the soldered portions.

According to the second embodiment of the present invention, since the lead wire intruding position into the soldering portion is obtained, thereby to judge the soldered state of the lead wire from the positional relation with respect to the soldered position, it becomes possible to prevent disengagement or poor contact of the lead wire.

By the third embodiment of the present invention, due to the detection of the state of the tunnel-like cavity at the lead wire intruding position, faults such as slipping off of lead wires, etc. may be prevented.

Furthermore, by the fourth embodiment of the present invention, unnecessary remaining ends of the lead wire may be detected, and therefore, short-circuit with respect to other land portions or casing, etc. due to remaining lead wires, can also be prevented.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as included therein.

What is claimed is:

1. A soldering appearance inspection apparatus for detecting a faulty soldering at a soldered portion on a printed circuit board, said inspection apparatus comprising:

illuminating means for illuminating the soldered portion;

image pickup means for picking up an image of the soldered portion; and image processing means for (1) receiving the image picked up by said image pickup means, effecting a Hough conversion of a differentiation image of the picked up image to obtain a density distribution of the picked up image, and discriminating as a solder edge a location in which the density distribution changes from a region of equal density to a region of non-equal density, (2) determining, from the thus discriminated soldered edge, a region of the soldered portion from the picked up image, (3) determining a ratio of a size of a subregion of the soldered portion in which light illuminated thereon is subjected to regular reflection to a size of the region of the soldered portion, and (4) judging a faulty state of the soldering at the soldered portion based on the thus determined ratio.

2. A soldering appearance inspection apparatus for detecting a faulty soldering at a soldered portion on a printed circuit board, said inspection apparatus comprising:

illuminating means for illuminating the soldered portion;

image pickup means for picking up an image of the soldered portion; and image processing means for (1) receiving the image picked up by said image pickup means, (2) determining a region of the soldered portion from the picked up image, (3) determining a ratio of a size of a subregion of the soldered portion in which light illuminated thereon is subjected to regular reflection to a size of the region of the soldered portion, and (4) judging a faulty state of the soldering at the soldered portion based on the thus determined ratio;

wherein said image processing means includes:

lead wire position detecting means for detecting a position and direction of a lead wire at an outer side portion of the soldered portion;

differentiation processing means for obtaining a value of a variation in brightness along successive portions of the lead wire;

lead wire intruding position detecting means for detecting an intruding position of the lead wire into the soldering based on the value of the variation of brightness, wherein the intruding position is determined as being at a position in which the value of the variation in brightness ceases to be characterized as a curve having two crests and a valley therebetween; and lead wire soldered state discriminating means for discriminating a quality of a soldered state of the lead wire based on the lead wire intruding position with respect to the soldered portion.

3. A soldering appearance inspection apparatus for detecting a faulty soldering at a soldered portion on a printed circuit board, said inspection apparatus comprising:

illuminating means for illuminating the soldered portion;

image pickup means for picking up an image of the soldered portion; and image processing means for (1) receiving the image picked up by said image pickup means, (2) determining a region of the soldered portion from the picked up image, (3) determining a ratio of a size of a subregion of the soldered portion in which light illuminated thereon is subjected to regular reflection to a size of the region of the soldered portion, and (4) judging a faulty state of the soldering at the soldered portion based on the thus determined ratio;

wherein said image processing means includes:

binary coding means for binary coding a partial region which is centered at a lead wire intruding position by an intermediate value of a brightness of the soldering and a concave portion at a position where a lead wire intrudes into the soldering;

means for obtaining a binary projection at said partial region; and judging means which obtains a size and degree of circularity of said concave portion darkened by the binary coding based on maximum and minimum values of data obtained by dividing a projecting axis into at least three equal portions for judging whether or not said concave portion is of a tunnel-like cavity.

4. A soldering appearance inspection apparatus for detecting a faulty soldering at a soldered portion on a printed circuit board, said inspection apparatus comprising:

illuminating means for illuminating the soldered portion;

image pickup means for picking up an image of the soldered portion; and image processing means for (1) receiving the image picked up by said image pickup means, (2) determining a region of the soldered portion from the picked up image, (3) determining a ratio of a size of a subregion of the soldered portion in which light illuminated thereon is subjected to regular reflection to a size of the region of the soldered portion, and (4) judging a faulty state of the soldering at the soldered portion based on the thus determined ratio;

wherein said image processing means comprises:

differentiation processing means for obtaining a variation of brightness of a lead wire;

binary coding means for binary coding the differential processed image at levels higher than a predetermined level; and, remaining wire detecting means for judging a presence or absence of a binary image configuration having a feature of a lead wire located outside the soldering and present at a position which is different from a lead wire position.

* * * * *